United States Patent
Seeger Pfeiffer et al.

(10) Patent No.: US 8,846,376 B2
(45) Date of Patent: Sep. 30, 2014

(54) RECOMBINANT BACTERIUM CAPABLE OF REMOVING MERCURY (II) SPECIES, CADMIUM (II) AND COPPER (II) IN PRESENCE OF OTHER HEAVY METALS FROM POLLUTED SITES, PRODUCT FOR THE BIOREMEDIATION, PROCESS OF OBTAINING THE PRODUCT AND METHOD OF BIOREMEDIATION

(75) Inventors: Michael Seeger Pfeiffer, Valparaiso (CL); Luis Antonio Rojas Araya, Valparaiso (CL); Myriam Lydia Gonzalez Vergara, Valparaiso (CL); Carolina Elvira Maria Yañez Prieto, Valparaiso (CL)

(73) Assignee: Universidad Tecnica Federico Santa Maria (CL)

( * ) Notice: Subject to any disclaimer, the term of this patent is extended or adjusted under 35 U.S.C. 154(b) by 0 days.

(21) Appl. No.: 13/520,005

(22) PCT Filed: Dec. 20, 2010

(86) PCT No.: PCT/IB2010/055961
§ 371 (c)(1),
(2), (4) Date: Jun. 29, 2012

(87) PCT Pub. No.: WO2011/080663
PCT Pub. Date: Jul. 7, 2011

(65) Prior Publication Data
US 2012/0276615 A1 Nov. 1, 2012

(30) Foreign Application Priority Data
Dec. 30, 2009 (CL) .................................. 2234-2009

(51) Int. Cl.
| | |
|---|---|
| C12N 1/20 | (2006.01) |
| A62D 3/02 | (2007.01) |
| C12N 9/88 | (2006.01) |
| C12R 1/01 | (2006.01) |
| B09C 1/10 | (2006.01) |
| C12N 15/52 | (2006.01) |
| C12N 9/02 | (2006.01) |
| C02F 101/20 | (2006.01) |
| C02F 3/34 | (2006.01) |

(52) U.S. Cl.
CPC ... *B09C 1/10* (2013.01); *C12N 9/88* (2013.01);
*C12Y 116/01001* (2013.01); *C12R 1/01* (2013.01); *C02F 2101/20* (2013.01); *C12N 15/52* (2013.01); *C02F 3/34* (2013.01); *C12N 9/0091* (2013.01)
USPC ..................................... 435/262.5; 435/252.3

(58) Field of Classification Search
None
See application file for complete search history.

(56) References Cited

PUBLICATIONS

Bersch et al., J. Mol. Biol. (2008) 380, 386-403.*
Valls et al., Nature Biotechnology, vol. 18 Jun. 2000, pp. 661-665.*
Collard et al., FEMS Microbiology Reviews 14 (1994) 405-414.*
Reith et al., PNAS ,Oct. 20, 2009, vol. 106, No. 42, pp. 17757-17762.*
Tao et al., Int. J. Environ. Res. Public Health 2009, 6, 2470-2480.*
Smalla et al. "Increased abundance of IncP-1β plasmids and mercury resistance genes in mercury-polluted river sediments: first discovery of IncP-1β plasmids with a complex mer transposon as the sole accessory element." *Applied and Environmental Microbiol.* vol. 72. No. 11. 2006. pp. 7253-7259.
Monchy et al. "Plasmids pMOL28 and pMOL30 of *Cupriavidus metallidurans* are specialized in the maximal viable response to heavy metals." *J. of Bacteriology.* vol. 189. No. 20. 2007. pp. 7417-7425.
Von Rozycki et al. "*Cupriavidus metallidurans* evolution of metal-resistant bacterium." *Antonie Van Leeuwenhoeke.* vol. 96. 2009. pp. 115-139.
International Search Report for International Application No. PCT/IB2010/055961 mailed Jul. 5, 2011.
Rojas et al., "Characterization of the Metabolically Modified Heavy Metal-Resistant *Cupriavidus metallidurans* Strain MSR33 Generated for Mercury Bioremediation", PLoS ONE, www.plosone.org, Mar. 2011, vol. 6, Issue 3, 10 pages.

* cited by examiner

*Primary Examiner* — Irene Marx
(74) *Attorney, Agent, or Firm* — Merchant & Gould P.C.

(57) ABSTRACT

A heavy metal-resistant recombinant bacterium capable to remove mercury (II) species, cadmium and copper (II) in presence of other heavy metals from polluted sites, which corresponds to *Cupriavidus metallidurans* strain MSR33, deposited under the access number NRRL B-50299, a product for the bioremediation of environments contaminated with heavy metals, where the product includes a bacterial inoculum of this recombinant strain, the process of obtaining the product and a method for the bioremediation of environments contaminated with heavy metals, which uses this product for the bioremediation.

12 Claims, 8 Drawing Sheets

RECOMBINANT BACTERIUM CAPABLE OF REMOVING MERCURY (II) SPECIES, CADMIUM (II) AND COPPER (II) IN PRESENCE OF OTHER HEAVY METALS FROM POLLUTED SITES, PRODUCT FOR THE BIOREMEDIATION, PROCESS OF OBTAINING THE PRODUCT AND METHOD OF BIOREMEDIATION

This application is a National Stage Application of PCT/IB2010/055961, filed 20 Dec. 2010, which claims benefit of Serial No. 2234-2009, filed 30 Dec. 2009 in Chile and which applications are incorporated herein by reference. To the extent appropriate, a claim of priority is made to each of the above disclosed applications.

The present invention relates to the heavy-metal removal recombinant bacterium *Cupriavidus metallidurans* MSR33, deposited under the access number NRRL B-50299. This novel bacterium strain is capable to remove inorganic and organic forms of mercury (II) as well cadmium (II) and copper (II) from contaminated soils, water bodies or industrial wastes. The incorporation of novel mer genes provides strain MSR33 with an additional high resistance to organomercurial compounds, inorganic mercury and cadmium and maintained resistances to other heavy metals such as copper of the native bacterial strain. The invention also relates to a product for the bioremediation which contains this bacterium, a process of obtaining the product and a method for bioremediation of heavy metal-polluted environments with *Cupriavidus metallidurans* strain MSR33 NRRL B-50299.

BACKGROUND OF THE INVENTION

Heavy metals such as copper, nickel, zinc and cobalt are nutrients that play important biological roles at low concentrations. However, they become toxic to the organisms at high concentrations. Other heavy metals such as mercury, cadmium and lead have no function in the living organisms and are highly toxic at low concentrations.

The maximum acceptable concentrations established by the Ministry of the Environment of Quebec (Ministère de l'Environnement du Québec, 1998, politique de protection des sols et de réhabilitation des terrains contaminés) for mercury, cadmium and copper are 0.2, 1.5 and 40 µg/g respectively.

The heavy metals present in contaminated soils and waters come from natural and anthropogenic sources either by mining or other activities such as the production of electricity using fossil fuels.

The presence of heavy metals such as mercury in domestic waters, industrial waste waters, and in agricultural soils has increased in recent decades and is a major cause of contamination. This is of increasing concern due to the high toxicity of mercury for living cells.

Mercury contamination of water occurs mainly by atmospheric deposition such as rainfall and runoff from industrial waste waters where mercuric ion $Hg^{2+}$ is the main form of mercury.

The deposition of mining waste rich in minerals, copper smelters, incineration emissions, and combustion of fossil fuels are important anthropogenic activities that contaminate large soil areas with toxic elements. According to the Environmental Protection Agency (EPA) from U.S.A., in 2007 gold mining accounts for 18% of anthropogenic mercury emissions to the soil.

The ionic mercury can be methylated by microorganisms to produce methylmercury ($MeHg^+$). Methylmercury is the most toxic mercury (II) species and represents a public health problem. The bioaccumulation and biomagnification of mercury in the food chain could be a risk for human health. The risks associated with mercury contamination have increased the restrictions to this heavy metal in liquid industrial wastes, where the maximum acceptable concentration in Europe is ≤50 ng/g.

Mercury species are toxic. The exposure to mercury could cause severe neurological diseases and the death. Organomercurial compounds are the most toxic chemical forms of Hg (II).

The mining activities and gold extraction are main sources of mercury contamination in soils. Gold mining in large-scale and artisanal mining, which is widely distributed in the world use mercury to extract gold. As a consequence, mercury may pollute soils, affecting human health and the environment.

Cadmium toxicity is caused by the decrease of glutathione and its interaction with sulfhydryl groups of proteins. Exposure to cadmium can cause chronic lung diseases, and kidney diseases, hypertension and bone disorders. Cadmium affects the calcium metabolism. Cadmium inhibits the activation of vitamin D and decreases the absorption of calcium and consequently the bone mineralization.

Cadmium moves easily in the environment from soil to plants by root absorption, thus entering the food chain affecting the human health.

Copper is an essential micronutrient widely distributed in nature. Copper is an essential component of many enzymes such as oxidases. The acute or chronic ingestion of copper salts may cause hepatic necrosis and the death. Copper contamination comes mainly from mining activities and the application of pesticides, fungicides and algaecides. As a result of mining activities, agricultural soils have been contaminated with significant levels of copper. Copper moves from soil to animals and humans through the food chain.

Heavy metals can be removed from contaminated sites by physicochemical processes such as ion exchange by columns, adsorbents such as activated carbon, chemical precipitation, filtration processes, etc. These processes are not selective and require further treatment that involves expensive and regeneration processes. Generally, physicochemical processes may involve the production of more toxic compounds either by concentration processes or by formation of new products by applying chemicals for precipitation, coagulation and flocculation.

Mercury removal by biological methods such as bacterial bioremediation is an attractive alternative to physicochemical treatments. This alternative has shown to be robust with relatively low cost on an industrial scale when it has been applied to industrial waste liquids from chloro-alkali manufacturing. The biological removal of mercury is highly selective and efficient and can minimize the final volume of the pollutant for final disposal.

Microorganisms such as bacteria are involved in the global mercury cycle by reducing chemical forms of Hg(II) ($Hg^{+2}$, $MeHg^+$) to the metallic form $Hg^0$. Reduced mercury ($Hg^0$) is less soluble in aqueous systems and therefore, is less bioavailable. Metallic mercury is the less toxic form of all mercury species. The biotechnological application of mercury removal from contaminated water and soil includes the biotransformation of the toxic mercury (II) in the reduced form and the collection of mercury from the gas phase in an oxidizing solution. Mercury is re-oxidized and then could be precipitated with alkali or sulfide.

Reduction of mercury (II) forms to elemental mercury is widely distributed in Gram-positive and Gram-negative bacteria. Genes responsible for metal uptake and reduction are organized in operons present in plasmids and transposons. The merRTPABD cluster is a typical mer operon in Gram-negative bacteria, which confers resistance to mercury compounds. Mercury induces the expression of structural genes merTPABD. The expression of the mer genes is regulated by a transcriptional regulator encoded by the merR gene. MerR is a transcriptional regulator of the mer operon which acts as a repressor or activator in the absence or presence of mercury, respectively. MerD is a protein that is synthesized by the cell when the mercury has been completely removed from the cytoplasm and acts as a distal regulator. MerP is a periplasmic protein that captures extracellular mercury and transfer it to the MerT membrane protein, which delivers Hg(II) to the cytosolic protein MerA (mercuric reductase) that enzymatically reduces the ionic mercury to the metallic state. MerB is an organomercurial lyase that catalyses the protonolytic cleavage of carbon-mercury bonds in organomercurial compounds releasing Hg (II) for the reduction by MerA. The mer operon lacking the merB gene is classified as narrow-spectrum operon, and confers only a low resistance to inorganic mercury salts and not resistance to organomercurial compounds. The mer operon that contains the gene merB is classified as a broad-spectrum operon that confers resistance to both inorganic and organic mercury species. In a recent study, a plasmid (pTP6) was exogenously isolated from a site contaminated with mercury in the river Nura, Kazakhstan. The pTP6 plasmid carries a complex mer transposon as sole accessory element (Smalla K. et al. en "Increased abundance of IncP-1 beta plasmids and mercury resistance genes in mercury-polluted river sediments: First discovery of IncP-1 beta plasmids with a complex mer transposon as the sole accessory element". *Appl Environ Microbiol* 2006, 72:7253-7259). The plasmid pTP6 is an IncP-1β type plasmid that has acquired a transposon (Tn50580) encoding broad-spectrum mercury resistance genes. The mercury resistances genes that are present in Tn50580 of plasmid pTP6 are merR1, merT, merP, merA, merG, merB1: merR2, merB2, merD2 and merE.

Mercury-contaminated sites by mining activities often are polluted with other heavy metals such as cadmium and copper. For bioremediation of heavy metals such as mercury, cadmium and copper, a wide range heavy metal-resistant microorganism should be used.

The strain of this invention is useful for this technical challenge. The bacterium *Cupriavidus metallidurans* strain MSR33 is useful for the removal of mercury as well cadmium and copper from contaminated sites. *Cupriavidus metallidurans* strain MSR33, is a recombinant bacterial strain generated by incorporation of the natural plasmid pTP6 into the native strain *Cupriavidus metallidurans* CH34. This plasmid confers to the native strain a broad-spectrum mercury resistance and also an increased cadmium resistance, maintaining the copper resistance. Plasmid pTP6 is a natural plasmid that contains mercury resistances genes in the transposon Tn50580 conferring a broad-spectrum resistance. The mercury resistance genes that are present in Tn50580 of plasmid pTP6 are merR1, merT, merP, merA, merG, merB1: merR2, merB2, merD2 and merE.

*Cupriavidus metallidurans* (formerly *Wautersia metallidurans, Ralstonia metallidurans, Alcaligenes eutrophus*) strain CH34 is a native metal-resistant bacterium isolated from a zinc decantation tank (Mergeay et. al. in "*Alcaligenes eutrophus* CH34 is a facultative chemolithotroph with plasmid-bound resistance to heavy metals". *J Bacteriol* 1985, 162:328-334, von Rozycki et. al. in "*Cupriavidus metallidurans*: evolution of a metal-resistant bacterium". Antonie Van Leeuwenhoek 2009, 96:115-39). *Cupriavidus metallidurans* CH34 has two plasmids: pMOL28 (171 kb) and pMOL30 (234 kb), containing several genetic determinants of heavy metal resistance. The genes involved in Hg(II), Co(II), Cr(VI) and Ni(II) resistance are located in a 34-kb region on pMOL28 and genes involved in Hg (II), Cd (II), Cu (II), Ag (I), Co (II), Pb (II) and Zn (II) resistance are located in a 132-kb region on pMOL30. Each plasmid possesses mercury determinants of narrow spectrum (i.e. have only a slight resistance to inorganic mercury). The operons merRTPAD are present in the transposons Tn4378 (pMOL28) and Tn4380 (pMOL30). Mercury bioremediation of contaminated sites using *Cupriavidus metallidurans* CH34 has not been reported.

DESCRIPTION OF THE INVENTION

The present invention relates to a mercury removing recombinant strain, *Cupriavidus metallidurans* MSR33, NRRL B-50299, which is capable to remove mercury, cadmium and copper from contaminated soils and sediments, waste waters and industrial waste waters contaminated with the these heavy metals and also other heavy metals. *Cupriavidus metallidurans* MSR33 has been deposited with the Agricultural Research Culture Collection (NRRL) International Depositary Authority, 1815 N. University Street, Peoria, Ill. 61604 under the access number of NRRL B-50299 on Jul. 7, 2009, according to the Budapest Treaty.

The novel strain *Cupriavidus metallidurans* MSR33 is capable to remove inorganic and organic chemical forms of Hg (II). The heavy metals are selected from mercury (II) species such as mercuric chloride and methylmercuric chloride, cadmium (II), and copper (II).

In a second embodiment the strain of the present invention, *Cupriavidus metallidurans* MSR33 NRRL B-50299, is capable of reducing divalent mercury to elemental mercury producing volatilization thereof. At the same time, *Cupriavidus metallidurans* MSR33 NRRL B-50299 removes cadmium (II) and copper (II) by biosorption and bioprecipitation.

In an additional embodiment, this strain *Cupriavidus metallidurans* MSR33 NRRL B-50299, is capable of volatilizing different forms of mercury in the presence of sodium or potassium thioglycolate (mercaptoacetate).

The present invention also includes a method for the treatment or bioremediation of an environment contaminated with mercury (inorganic or organic mercury (II) species), cadmium and copper in presence of other heavy metals, wherein this method comprises the stages of i) adding the recombinant bacterium *Cupriavidus metallidurans* strain MSR33 to this contaminated environment, where this bacterium is capable of reducing Hg(II) to the metallic form and volatilize this element, and to remove cadmium and copper and ii) incubating this bacterium in the contaminated environment during a period from 1 hour to 4 weeks to permit the removal of mercury, cadmium and copper in the environment, and the bioremediation of thereof. In addition, the present invention includes a method to improve the bioremediation of the contaminated environment with chemical forms of mercury, cadmium and copper, where this method comprises the stages i) adding the recombinant bacterium that was previously cultivated in the presence of an inducer of mer genes to this contaminated environment and ii) incubating in the contaminated environment during a period of time from 1 hour to 4 weeks to permit the reduction and volatilization of different chemical forms of mercury present in the environment, and the removal of cadmium and copper, thereby obtaining the removal or bioremediation of the contaminated environment.

DETAILED DESCRIPTION OF THE INVENTION

Figure 1:
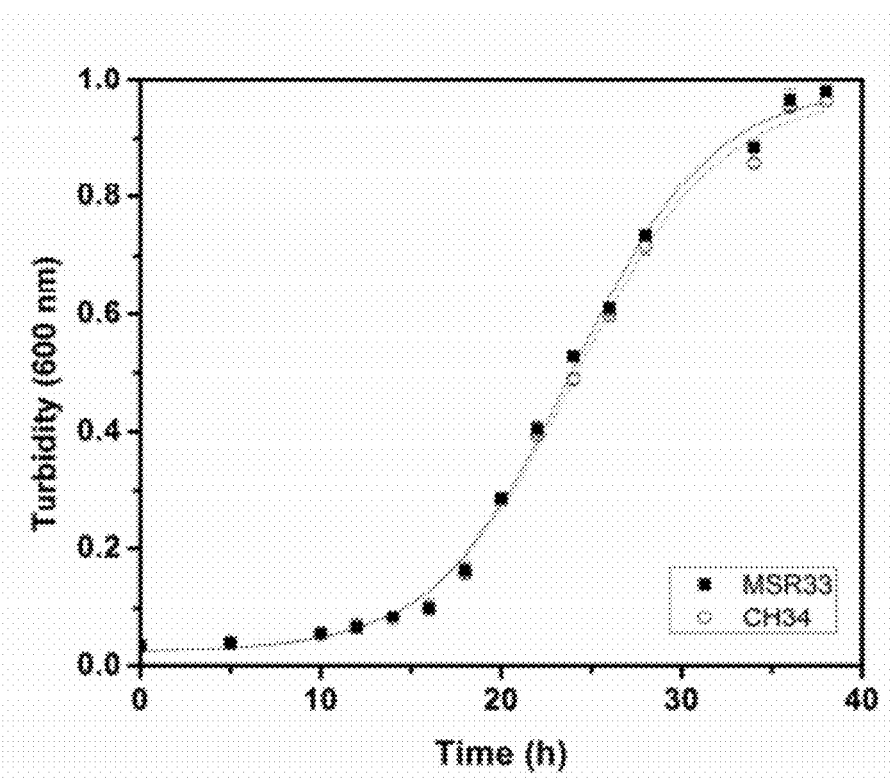
FIG. 1 shows the growth of the strain *Cupriavidus metallidurans* MSR33 in Tris mineral salts medium in absence of mercury. The growth of strain *Cupriavidus metallidurans* CH34 in the same medium is also shown.

The present invention is related to a recombinant bacterium, *Cupriavidus metallidurans* MSR33, deposited under accession number NRRL B-50299 which is capable to remove different mercury (II) chemical forms, cadmium and copper in presence of other heavy metals, a product for bioremediation, a process for obtaining the product, and a method of bioremediation of environments contaminated with different chemical forms of mercury (II), cadmium and copper and other heavy metals. This bacterium is generated based on the incorporation of the natural plasmid pTP6 carrying a complex set of mer genes (Smalla K. et al. in "Increased abundance of IncP-1 beta plasmids and mercury resistance genes in mercury-polluted river sediments: First discovery of IncP-1 beta plasmids with a complex mer transposon as the sole accessory element". *Appl Environ Microbiol* 2006, 72(11):7253-7259) into the model heavy metal-resistant bacterium *Cupriavidus metallidurans* CH34 (Mergeay et al. in "*Alcaligenes eutrophus* CH34 is a facultative chemolithotroph with plasmid-bound resistance to heavy metals". *J Bacteriol* 1985, 162: 328-334, von Rozycki et al. in "*Cupriavidus metallidurans*: evolution of a metal-resistant bacterium". Antonie Van Leeuwenhoek 2009, 96:115-39).

DEFINITIONS

As used in the present invention the term "volatilization" refers to the mercury extraction from contaminated sites, and its subsequent reduction from the divalent form to the metallic form that is in gaseous state by enzymes encoded by mer genes.

As used in the present invention the term "heavy metal" refers to the metallic chemical element whose density is greater than 7 g/ml such as mercury, cadmium and copper.

As used in the present invention the term "biosorption" represents the extraction of heavy metals from contaminated sites by bacteria and their incorporation into the outer cell membrane by adsorption.

As used in the present invention the term "bioprecipitation" represents the extraction of heavy metals from contaminated sites by bacteria and their incorporation into the cell and later exportation to the outer membrane where the heavy metals are precipitated by carbonates and bicarbonates.

As used in the present invention the term "bioremediation" means the treatment method for a contaminated environment or contaminated waste material located in a specific environment, where said treatment allows the transformation of this waste material into a less toxic material or the removal of the pollutant by a microorganism or a group of microorganisms, where this treatment method comprises the application of a living organism as a component of the treatment method.

As used in the present invention the term "native" referred to a bacterial strain represents a natural bacteria which has not been modified by foreign deoxyribonucleic acid.

As used in the present invention the term "recombinant bacterium" is referred to a bacterial strain which has incorporated foreign deoxyribonucleic acid by conjugation. Deoxyribonucleic acid may be a circular plasmid which is incorporated into a host cell by conjugation or transformation.

As used in the present invention the term "*Cupriavidus metallidurans* NRRL B-50299 MSR33" is considered equivalent to "*Cupriavidus metallidurans* MSR33", to "MSR33" and to "NRRL B-50299", and any of these terms can be used indistinctly to refer to the strain of the invention.

*Cupriavidus metallidurans* MSR33 is a recombinant strain derived from *Cupriavidus metallidurans* CH34 but with improved capabilities for the bioremediation of heavy metals such as mercury and cadmium, maintaining its copper removal capability. The strain *Cupriavidus metallidurans* CH34 is a Gram-negative bacterium isolated in zinc decantation tank in Belgium at late 1970s, characterized by its capability to resist different heavy metals. This strain is one of the model microorganisms used for heavy metal resistance studies. The heavy metal genetic determinants have been extensively studied, and the genome of this bacterium has been sequenced. *Cupriavidus metallidurans* CH34 has two plasmids: pMOL28 (171 kb) and pMOL30 (234 kb), containing several genetic determinants of heavy metal resistance. The genes involved in Hg(II), Co(II), Cr(VI), and Ni(II) resistance are located in a 34-kb region on pMOL28 and the genes involved in Hg (II), Cd (II), Cu (II), Ag (I), Co (II), Pb (II) and Zn (II) resistance are located in a 132-kb region on pMOL30. Each plasmid possesses mercury determinants of narrow spectrum (i.e. have only a slight resistance to inorganic mercury). The operons merRTPAD are present in the transposons Tn4378 (pMOL28) and Tn4380 (pMOL30). The strain *Cupriavidus metallidurans* MSR33 was obtained by incorporating through biparental mating the natural IncP-1beta plasmid pTP6, which is carrying a complex set of mer genes, merR1TPAGB1, merR2B2D2E present in the transposon Tn50580 that confer broad spectrum mercury resistant to the host strain.

Construction of *Cupriavidus metallidurans* Strain MSR33

Strain MSR33 of this invention was obtained by the incorporation of pTP6 plasmid into the CH34 host strain. The presence of plasmid pTP6 in the strain MSR33 add new mercury resistance genes such as two copies of merB genes and one copy of merG that confer resistance to organomercurial compounds. Additional copies of mercury resistance genes such as merT, merP, merA, merD and merE genes already present in the native strain CH34 improved inorganic mercury resistance. All the mer genes incorporated are present in the plasmid pTP6 which possesses only a mercury resistance transposon and not antibiotic resistance or organic compounds catabolic genes. The plasmid pTP6 was transferred to the strain CH34 through biparental mating, which is a well known technique in the state of the art. The plasmid pTP6 was transferred by conjugation from donor cells, *Eschericha coli* strain JM109 which contains the plasmid pTP6 to the recipient cells, *Cupriavidus metallidurans* CH34. The recombinant strain, *Cupriavidus metallidurans* MSR33 NRRL B-50299 showed a novel resistance to organomercurial compounds, and an improved resistance to inorganic $Hg^{2+}$ and $Cd^{2+}$, maintaining the original copper resistance. For an expert in the art is evident that there are other methods to transfer the plasmid pTP6 to the host strain CH34. Conjugation, transformation, electroporation could be used for plasmid transfer to obtain *Cupriavidus metallidurans* NRRL B-50299 MSR33.

Description of the *Cupriavidus metallidurans* Strain MSR33

The novel strain *Cupriavidus metallidurans* MSR33 has novel merB genes encoding for the organomercurial lyase and a merG gene encoding for a protein involved in phenylmercury transport. The genes merB and merG confer resistance to organomercurial compounds. *Cupriavidus metallidurans* MSR33 also has additional mercury resistance genes that confers a high resistance to inorganic forms of Hg(II), such as merP, merT, merA and merD genes, and a novel merE gene that is involved in the transport of inorganic and organic forms of Hg(II).

The increase of the heavy metal resistance of the novel strain *Cupriavidus metallidurans* MSR33 was confirmed measuring minimum inhibitory concentration (MIC) of heavy metals in agar plates containing Tris mineral salts medium supplemented with increasing heavy metal concentrations and the organomercurial compound methylmercury.

The incorporation of the plasmid pTP6 to the strain MSR33 increased MIC for $Hg^{2+}$ to 24 µg/g, MIC for $CH_3Hg^+$ to 18 µg/g and MIC for $Cd^{2+}$ to 160 µg/g. The parental strain CH34 showed a MIC for $Hg^{2+}$ of 10 µg/g, a MIC for $Cd^{2+}$ of 100 µg/g and was sensitive to $CH_3Hg^+$. The MIC for Cu was 240 µg/g for both strain MSR33 and CH34 (Table 1).

The incorporation of gen merB in strain MSR33 was confirmed by Polymerase Chain Reaction (PCR), which is a technology used for amplifying DNA well known in the state of art, using specific primers for merB gene amplification.

TABLE 1

| Metals | Strains | | Improved |
|---|---|---|---|
| (µg/g) | MSR33 | CH34 | resistance (fold) |
| $MeHg^+$ | 18 | <1 | >18.0 |
| $Hg^{2+}$ | 24 | 10 | 2.4 |
| $Cd^{2+}$ | 160 | 100 | 1.6 |
| $Cu^{2+}$ | 240 | 240 | — |

The stability of the mercury resistance phenotype of the strain MSR33 was studied during 100 generations. Strain MSR33 was grown in LB medium in absence of Hg (II). Grown liquid cultures of the strain MSR33 were sampled each 10 generations and diluted and plated in PCA medium. Colonies (48) were taken randomly and plated in PCA medium supplemented with Hg(II) (100 µg/g). To confirm that the resistance was due to the presence of plasmid pTP6 and discarding a recombination event, the presence of pTP6 was confirmed by plasmid extraction from the colonies.

The recombinant strain of the present invention, *Cupriavidus metallidurans* MSR33 showed that 100% of the colonies were mercury resistant after 70 generations, and 80% of the colonies were mercury resistant after 100 generations. The presence of plasmid pTP6 was observed in all selected colonies of strain MSR33 after growth during 70 and 100 generations under non selective conditions.

To characterize the novel mercury resistance capabilities, the recombinant strain *Cupriavidus metallidurans* MSR33 was grown in minimal medium supplemented with succinate as sole carbon source and energy and in the presence or absence of mercury. *Cupriavidus metallidurans* strain CH34 was also grown in these conditions.

Figure 2:
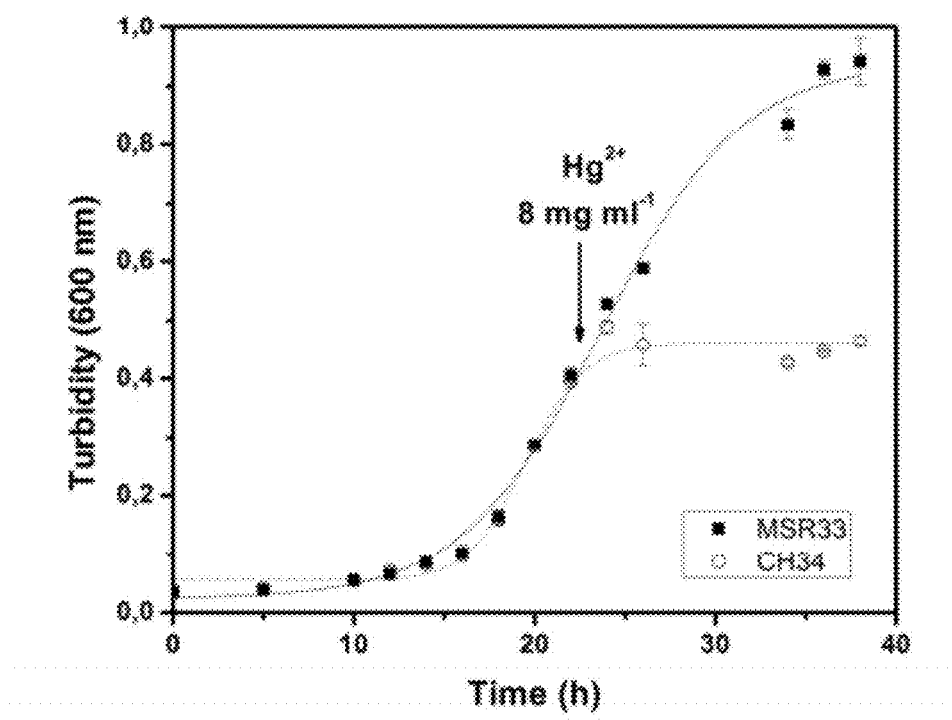
FIG. 2 shows the effect of addition of $Hg^{2+}$ (8 μg/g) at mid-exponential phase on the growth of *Cupriavidus metallidurans* strain MSR33 in Tris mineral salts medium. The effect of addition of $Hg^{2+}$ (8 μg/g) at mid-exponential phase on the growth of *Cupriavidus metallidurans* strain CH34 is also shown.
Figure 3:
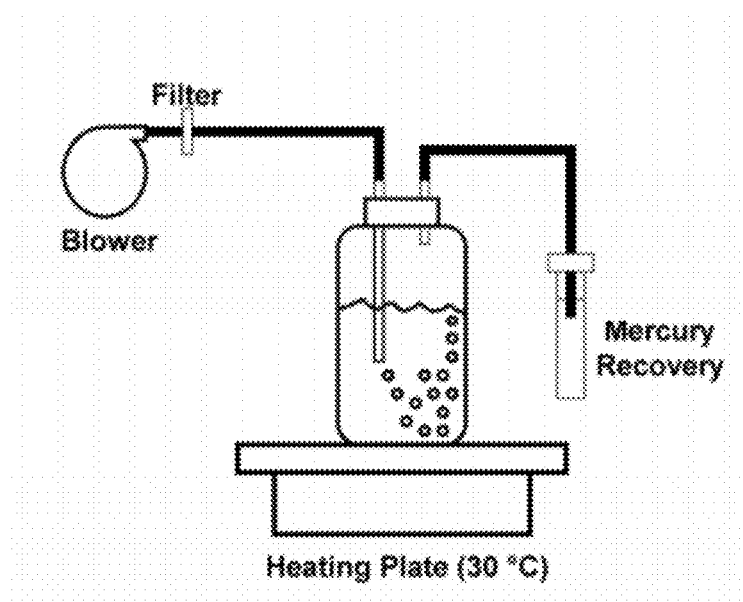
FIG. 3 shows the bioreactor used for the removal of heavy metals in water, sludge and soil by strain *Cupriavidus metallidurans* MSR33. This bacterium is added to the bioreactor. The bioreactor is maintained at 30° C. and agitated by an external aeration system. Volatilized mercury recovery is performed in a 10% $HNO_3$ trap that re-oxidized the mercury.

FIG. 1. shows the growth observed of strains MSR33 and CH34 in Tris mineral salts minimal medium. The growth of both strains is similar in absence of Hg (II). The addition of Hg (II) (8 µg/g) at mid-exponential phase do not affect the growth of *Cupriavidus metallidurans* MSR33 (FIG. 2.). In contrast, no further growth of strain CH34 was observed when $Hg^{2+}$ (8 µg/g) were added at exponential phase.

Furthermore, the present invention relates to a product for the bioremediation of heavy metal-polluted environments, which includes a bacterial inoculum of the strain of this invention, *Cupriavidus metallidurans* MSR33. The product for bioremediation contains an inoculum of *Cupriavidus metallidurans* MSR33 at a concentration range from about $10^4$ to $10^{12}$ cells/ml in a culture medium, a neutral saline medium or a neutral buffered solution.

In an additional embodiment, the product for the bioremediation of heavy metal-polluted environments includes a bacterial inoculum of the strain *Cupriavidus metallidurans* MSR33 NRRL B-50299, where the bacterial cells are lyophilized, which facilitates its transport and commercialization.

In an additional embodiment, the product for the bioremediation of heavy metal-polluted environments includes a bacterial inoculum of the strain *Cupriavidus metallidurans* MSR33 NRRL B-50299, where the bacterial cells are encapsulated in alginate. The encapsulation protects the bacterial cells and decreases its exposure to toxic compounds, increasing its stability and viability.

In an additional embodiment, the invention provides a treatment method for the bioremediation of an environment contaminated with mercury compounds and other heavy metals such as cadmium and copper. Environments such as soils, slurries, sediments and water contaminated with mercury compounds and other heavy metals are included in the invention.

In one embodiment of the invention, the bioremediation method includes the addition of a *Cupriavidus metallidurans* MSR33 culture to the heavy metal-polluted environment. The method of the invention includes a certain period of time from 1 hour to 4 weeks to permit the recombinant bacterium to remove mercury compounds and other heavy metals such as cadmium and copper.

For example, the recombinant bacterium *Cupriavidus metallidurans* MSR33 NRRL B-50299 can be added to an environment contaminated with mercury compounds and other heavy metals such as cadmium and copper, as an inoculum containing from about $10^4$ to $10^{12}$ cells/ml in a culture medium, a neutral saline medium or a neutral buffered medium. Then, this bacterial strain is incubated in the heavy metal-polluted environment during a period of time from about 1 hour to 4 weeks, depending of the matrix properties to allow that mercury species can be volatilized and the other heavy metals such as cadmium and copper can be removed.

In an additional embodiment, the bioremediation process described above may be monitored periodically, sampling and digesting the heavy metal-polluted environments with concentrated acids and heat for heavy metal extraction and analyzing the presence and quantity of heavy metals by emission spectroscopy or atomic absorption.

In an additional embodiment, the recombinant bacterium of the present invention can be cultivated with a compound that increases the mercury volatilization potential of this recombinant bacterium, e.g., a compound that induces the expression of mer genes for a more efficient bioremediation of mercury compounds. For example, the inducer could be inorganic $Hg^{2+}$ or $Cd^{2+}$ or both.

In an additional embodiment, the recombinant bacterium *Cupriavidus metallidurans* MSR33 of the present invention can be added to the heavy metal-polluted environments, with a compound that increases the mercury volatilization for a more efficient heavy metal bioremediation. For example, this compound can be sodium or potassium thioglycolate.

In a further embodiment, the above described contaminated environment is a matrix extracted from a contaminated environmental site, and relocated in a contained system. A contained system is a space, where the contaminated matrix does not have direct contact with the surrounding environment.

In the present invention, the term "microcosms" refers to a certain volume of water, slurry or soil in a container (flask) whose important variables such as moisture, density, presence or absence of microorganisms and/or pollutants such as heavy metals are known and controlled. The strain of the present invention *Cupriavidus metallidurans* MSR33 NRRL B-50299 has solved the problem of mercury (II) species removal in the presence of other heavy metals from contaminated sites using a bioremediation process.

Example 1

Inorganic Mercury Removal from Polluted Water by *Cupriavidus metallidurans* MSR33

The capability of the strain MSR33 to remove inorganic mercury from a contaminated water was evaluated. Kinetics of inorganic mercury removal from a solution of 50 ml containing $Hg^{2+}$ (20 µg/g) in phosphate buffer 50 mM in a bioreactor were performed. The system was composed of a plastic flask of 250 ml, aerated with an air pump with a constant flow of 300 ml/min, an exit for volatilized mercury and a trap containing 10% $HNO_3$ for metallic mercury recovery. The system was kept at 30° C. during all the process.

The inoculum was obtained by culturing the strain MSR33 until early stationary phase (turbidity at 600 nm of 1.1) equivalent to an approximate concentration of $10^9$ cells per ml. Bacteria were grown in Tris mineral medium using succinate as sole carbon and energy source. The culture was supplemented with $Hg^{2+}$ (2 µg/g) as inducer of mer genes. Grown cells were harvested and concentrated 10 times by centrifugation. The concentrated cells were added to the contaminated water containing inorganic $Hg^{2+}$ (20 µg/g) in a ratio of 1:10 and were incubated during 5 h.

Samples were taken at different incubation times and were centrifuged to separate the supernatant from the cells. The residual inorganic mercury present in the supernatant was measure by an Inductively coupled plasma atomic emission spectrometer with optical emission detector (ICP-OES, Perkin Elmer, Optima 2000 series) with hydride generation forming a cold vapor of metallic mercury (CV-ICP-OES).

To evaluate the effect of thioglycolate on mercury removal, experiments were carried out in absence or presence of 5 mM of thioglycolate. All assays were done in triplicate.

Figure 4:
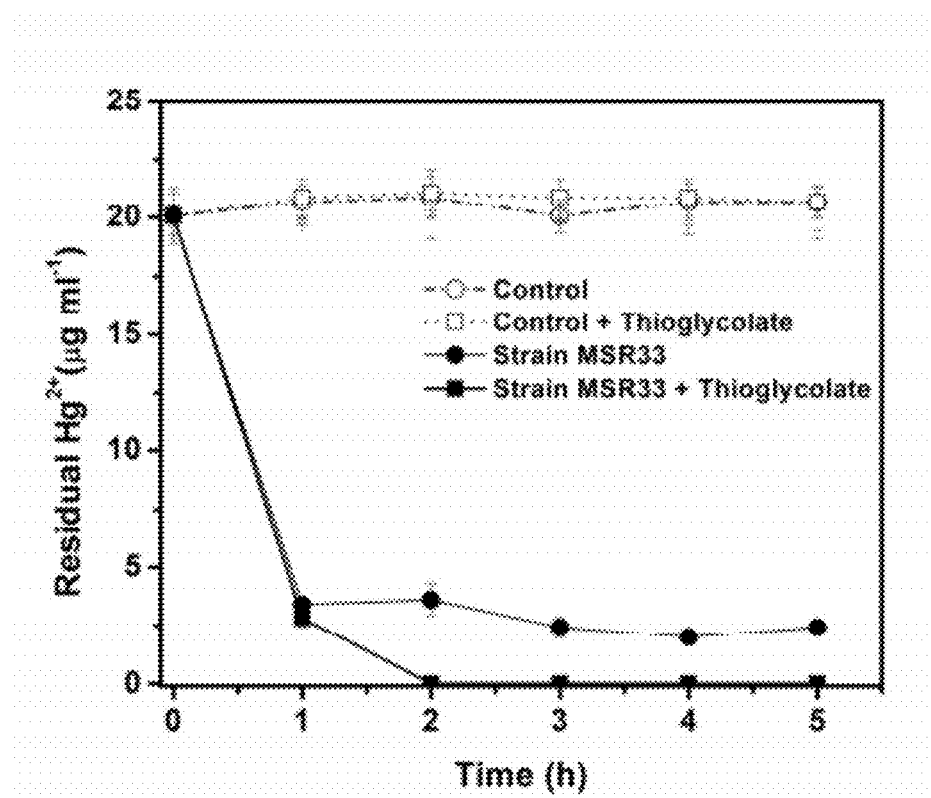
FIG. 4 shows the kinetic of mercury removal from a water contaminated with $Hg^{2+}$ (20 μg/g) by *Cupriavidus metallidurans* MSR33 at a final concentration of $5 \times 10^8$ cells/ml. In addition, the effect of thioglycolate on mercury removal was studied.

*Cupriavidus metallidurans* strain MSR33 removed completely inorganic mercury from contaminated water after 2 h in presence of thioglycolate. Eighty two per cent of mercury removal was observed in absence of thioglycolate. Inorganic mercury was not removed in absence of strain MSR33, either in absence or presence of thioglycolate. The mercury removal kinetics from contaminated water by strain MSR33 is shown in FIG. 4.

Example 2

Inorganic Mercury ($Hg^{2+}$) and Organic Mercury ($CH_3Hg^+$) Removal from Polluted Slurry by Bioremediation with *Cupriavidus metallidurans* MSR33

The capability of strain MSR33 to remove inorganic and organic mercury from a contaminated slurry was evaluated. Kinetics of mercury species removal were performed in a slurry prepared with 20 g of a soil with a density of 2 g/ml containing $Cu^{2+}$ (68 µg/g) and 100 ml of phosphate buffer 50 mM in a bioreactor of 500 ml. The slurry was spiked with mercury species obtaining a final concentration of $Hg^{2+}$ (40 µg/g) and $CH_3Hg^+$ (20 µg/g). The system was composed of a plastic flask of 500 ml, aerated with an air pump with a constant flow of 600 ml/min, an exit for gaseous mercury and a trap containing 10% $HNO_3$ for metallic mercury recovery. The system was kept at 30° C. during the process.

The inoculum was obtained by culturing strain MSR33 until stationary phase (turbidity measured at 600 nm of 1.1) equivalent to an approximate concentration of $10^9$ cells per ml. Bacteria were grown in Tris mineral medium using succinate as sole carbon and energy source. The culture was supplemented with $Hg^{2+}$ (2 µg/g) as inducer of the mer genes. Grown cells were harvested and concentrated 10 times by centrifugation. The concentrated cells were added to the contaminated slurry in a ratio of 1:10 and were incubated during 21 h. Thioglycolate was added to a final concentration of 5 mM.

Samples were taken at 0, 3, 5, 18 and 21 h. The residual total mercury present in the soil and buffer solution separated both by centrifugation was measure CV-ICP-OES. All assays were done in triplicate.

The results showed that strain MSR33 was capable to remove completely inorganic and organic mercury species from the contaminated slurry after 18 h. Removal of mercury species was not observed in presence of the native strain CH34.

Figure 5:
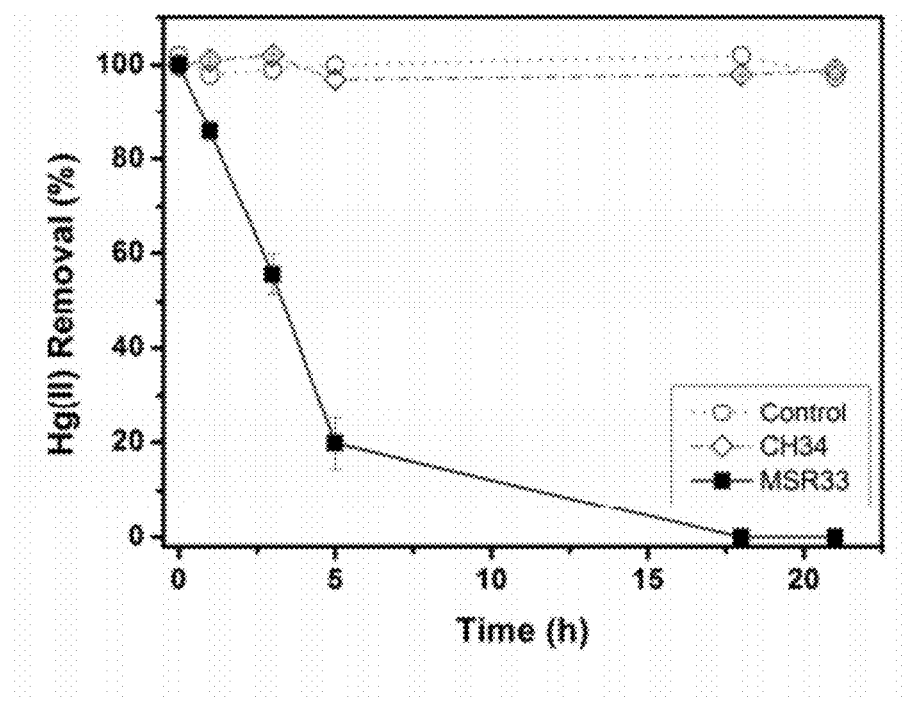
FIG. 5 shows the kinetic of mercury (II) species removal from a sludge contaminated with $Hg^{2+}$ (40 μg/g) and $CH_3Hg^+$ (methylmercury) (20 μg/g) by *Cupriavidus metallidurans* MSR33 at a final concentration of $5.2 \times 10^9$ cells/ml. Additionally, the effect of *Cupriavidus metallidurans* CH34 on mercury (II) species removal was also studied.

The total mercury removal kinetics from contaminated slurry by strain MSR33 is shown in FIG. 5.

Example 3

Removal of Mercury (II), Methylmercury, Cadmium and Copper from a Heavy Metal-Polluted Soil by Bioremediation with *Cupriavidus metallidurans* MSR33

The capability of the strain MSR33 to remove inorganic and organic mercury (II), cadmium and copper from a contaminated soil was evaluated. Kinetics of total inorganic mercury ($Hg^{2+}$ 23 µg/g) and organic mercury ($CH_3Hg^+$ 2 µg/g), cadmium ($Cd^{2+}$ 20 µg/g) and copper ($Cu^{2+}$ 68 µg/g) removal were performed in a soil. Microcosms were prepared in a bioreactor of 500 ml containing 20 g of soil with a density of 2 g/ml. The system was composed of a plastic flask of 500 ml, aerated with an air pump with a constant flow of 600 ml/min, an exit for volatilized mercury and a trap containing 10% $HNO_3$ for metallic mercury recovery. The system was kept at 30° C. during the process.

The inoculum was obtained by culturing strain MSR33 until early stationary phase (turbidity measured at 600 nm of 1.1) equivalent to an approximate concentration of $10^9$ cells per ml. Bacteria were grown in Tris mineral medium using succinate as sole carbon and energy source. The culture was supplemented with $Hg^{2+}$ (2 µg/g) as inducer of the mer genes. A volume of 100 ml of the liquid medium containing grown cells were added to the contaminated soil and incubated during 72 h.

Thioglycolate was added to a final concentration of 5 mM. Samples were taken at 0, 24, 48 and 72 h. The residual total mercury, cadmium and copper present in soil were measure by (CV)-ICP-OES.

The results showed that strain MSR33 was capable to remove a 77% of the total mercury, a 75% of cadmium and a 68% of copper from contaminated soil after 72 h.

Figure 6:
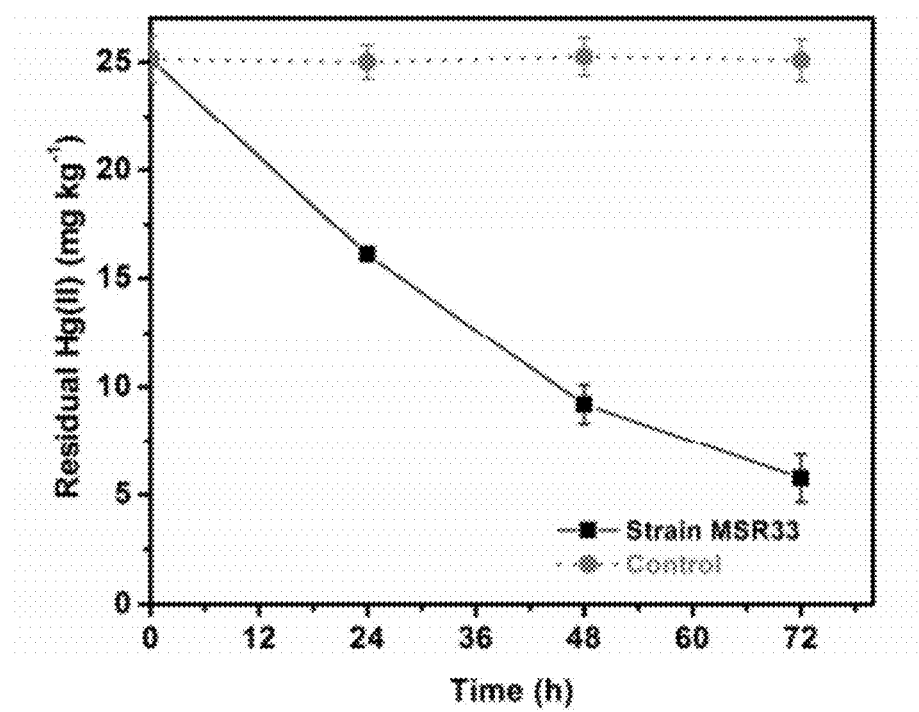
FIG. 6 shows the kinetic of mercury (II) species removal from a soil contaminated with $Hg^{2+}$ (23 μg/g) and $CH_3Hg^+$ (2 μg/g), cadmium ($Cd^{2+}$) (20 μg/g) and copper ($Cu^{2+}$) (68 μg/g) by *Cupriavidus metallidurans* MSR33 at a final concentration of $5.5 \times 10^9$ cells/ml.
Figure 7:
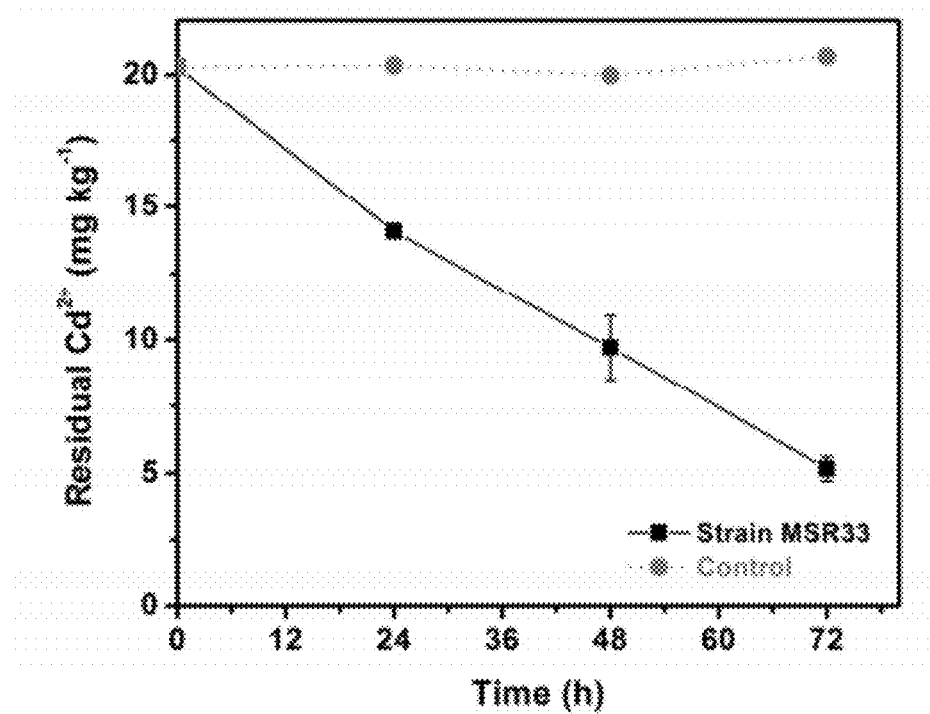
FIG. 7 shows the kinetic of cadmium removal from a soil contaminated with $Cd^{2+}$ (20 μg/g) in presence of mercury (II) species and copper by *Cupriavidus metallidurans* MSR33 at a final concentration of $5.5 \times 10^9$ cells/ml.
Figure 8:
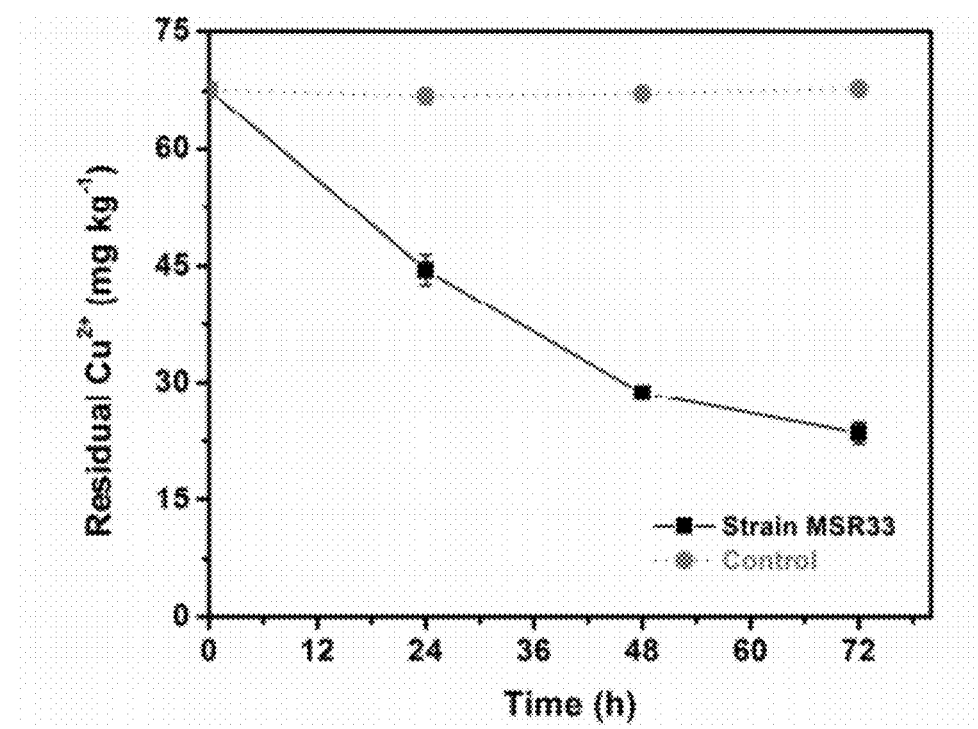
FIG. 8 shows the kinetic of copper removal from a soil contaminated with $Cu^{2+}$ (68 μg/g) in presence of mercury (II) species and cadmium by *Cupriavidus metallidurans* MSR33 at a final concentration of $5.5 \times 10^9$ cells/ml.

The total mercury, cadmium and copper removal kinetics from contaminated soil by strain MSR33 is shown in FIG. 6, FIG. 7 and FIG. 8.

REFERENCES

Mergeay M, Nies D, Schlegel H G, Gerits J, Charles P, Van Gijsegem F. *Alcaligenes eutrophus* CH34 is a facultative chemolithotroph with plasmid-bound resistance to heavy metals. *J Bacteriol* 1985, 162:328-334 von Rozycki T, Nies D H. *Cupriavidus metallidurans*: evolution of a metal-resistant bacterium. Antonie Van Leeuwenhoek 2009, 96:115-39

Smalla K, Haines A S, Jones K, Krögerrecklenfort E, Heuer H, Schloter M, Thomas C M. Increased abundance of IncP-1 beta plasmids and mercury resistance genes in mercury-polluted river sediments: First discovery of IncP-1 beta plasmids with a complex mer transposon as the sole accessory element. *Appl Environ Microbiol* 2006, 72:7253-7259

The invention claimed is:

1. A method for bioremediation of a heavy metal-contaminated environment, comprising:
    a) adding a bacterial inoculum comprising *Cupriavidus metallidurans* strain MSR33, deposited under accession number NRRL B-502099, to the heavy metal-contaminated environment, wherein said *Cupriavidus metallidurans* strain MSR33, NRRL B-50299 is capable of removing one or more heavy metals from said contaminated environment and said bacterial inoculum comprises an effective amount of said *Cupriavidus metallidurans* strain MSR33, NRRL B-502 for removing one or more heavy metals from said contaminated environment, and
    b) incubating said bacterial inoculum in said contaminated environment for a period of time ranging from 1 hour to 4 weeks to remove heavy metals from said contaminated environment.

2. The method according to the claim 1, wherein said heavy metal is organic mercury, inorganic mercury, cadmium, or copper.

3. The method according to claim 1, wherein incubation of said bacterial inoculum in the environment is performed in presence of thioglycolate.

4. A method for bioremediation of a mercury (II) species-contaminated environment, comprising:
    a) adding a bacterial inoculum comprising *Cupriavidus metallidurans* strain MSR33, deposited under accession number NRRL B-502099, to said mercury (II) species-contaminated environment in presence of sodium or potassium thioglycolate, wherein said *Cupriavidus metallidurans* strain MSR33, NRRL B-50299 is capable of removing mercury (II) species from said contaminated environment and said bacterial inoculum comprises an effective amount of said *Cupriavidus metallidurans* strain MSR33, NRRL B-502 for removing mercury (II) species from said contaminated environment, and
    b) incubating said bacterial inoculum in said contaminated environment for a period of time ranging from 1 hour to 4 weeks remove mercury (II) species from said contaminated environment.

5. A method for bioremediation of a cadmium-contaminated environments, comprising:
    a) adding a bacterial inoculum comprising *Cupriavidus metallidurans* strain MSR33, deposited under accession number NRRL B-502099, to the to the cadmium-contaminated environments wherein said *Cupriavidus metallidurans* strain MSR33, NRRL B-50299 is capable of removing cadmium from said contaminated environment and said bacterial inoculum comprises an effective amount of said *Cupriavidus metallidurans* strain MSR33, NRRL B-502 for removing cadmium from said contaminated environment, and
    b) incubating said bacterial inoculum in said contaminated environment for a period of time ranged from 1 hour to 4 weeks to remove cadmium from said contaminated environment.

6. A method for bioremediation of a copper-contaminated environments, comprising:
    a) adding a bacterial inoculum comprising *Cupriavidus metallidurans* strain MSR33, deposited under accession number NRRL B-502099, to said copper-contaminated environment, wherein said *Cupriavidus metallidurans* strain MSR33, NRRL B-50299 is capable of removing copper from said contaminated environment and said bacterial inoculum comprises an effective amount of said *Cupriavidus metallidurans* strain MSR33, NRRL B-502 for removing copper from said contaminated environment, and
    b) incubating said bacterial inoculum in said contaminated environment for a period of time ranging from 1 hour to 4 weeks to remove copper from said contaminated environment.

7. The method of claim 1, wherein said bacterial inoculum comprises from $10^4$ cells/ml to $10^{12}$ cells/ml of *Cupriavidus metallidurans* strain MSR33, NRRL B-50299.

8. The method according to claim 1, wherein said bacterial inoculum has been cultivated in presence of inorganic mercury (II) or cadmium (II) to induce mercury resistance genes or cadmium resistance genes in said *Cupriavidus metallidurans* strain MSR33, NRRL B-50299.

9. The method according to claim 1, wherein said bacterial inoculum contains lyophilized cells of said *Cupriavidus metallidurans* strain MSR33.

10. The method according to claim 1, wherein said bacterial inoculum contains alginate-encapsulated cells of said *Cupriavidus metallidurans* strain MSR33.

11. The method according to claim 4, wherein said bacterial inoculum contains lyophilized cells of said *Cupriavidus metallidurans* strain MSR33.

12. The method according to claim 4, wherein said bacterial inoculum contains alginate-encapsulated cells of said *Cupriavidus metallidurans* strain MSR33.

\* \* \* \* \*